United States Patent [19]
Root et al.

[11] Patent Number: 5,989,924
[45] Date of Patent: Nov. 23, 1999

[54] DEVICE FOR DETERMINING AN ANALYTE IN A SAMPLE

[75] Inventors: Richard T. Root, Kirkland, Wash.; Stephen J. Lovell, Lutherville, Md.

[73] Assignee: Becton, Dickinson and Company, Franklin Lakes, N.J.

[21] Appl. No.: 08/941,184

[22] Filed: Sep. 30, 1997

[51] Int. Cl.$^6$ .................... G01N 33/543; G01N 33/5588
[52] U.S. Cl. .............. 436/518; 422/55; 422/56; 422/58; 422/61; 436/164; 436/169; 436/514; 436/530; 436/805; 436/809; 436/810; 435/6; 435/287.1; 435/287.2; 435/287.7; 435/287.8; 435/287.9; 435/810
[58] Field of Search ............................. 422/55–58, 61; 435/6, 287.1, 287.2, 287.7, 287.8, 287.9, 810; 436/164, 169, 514, 518, 530, 805, 809, 810

[56] References Cited

U.S. PATENT DOCUMENTS 5,418,171  5/1995  Kimura et al. ............................ 436/518
5,474,902  12/1995  Uylen et al. ............................... 422/56

*Primary Examiner*—Christopher L. Chin
*Attorney, Agent, or Firm*—Bruce S. Weintraub

[57] ABSTRACT

The present invention relates to a device for determining an analyte in a fluid sample in an assay. The device comprises a lid having a plurality of elements and a membrane. The elements have openings which allow passage of fluid to the membrane. The membrane is supported by the lid and covers the openings of the elements. The undersurface of the membrane is in contact with a porous wick which contains a first zone which includes binder attached to a particulate label and a second zone containing salt. The wick extends downward from the membrane and is in contact with the fluid sample.

21 Claims, 4 Drawing Sheets

DEVICE FOR DETERMINING AN ANALYTE IN A SAMPLE

FIELD OF THE INVENTION

The present invention relates to a device for determining an analyte in a fluid sample in an immunoassay and its use thereof

BACKGROUND OF THE INVENTION

Immunoassay, which takes advantage of natural immunological reactions, is a well-recognized technique in quantifying biological analytes that are present in biological fluids. Such analytes include, but are not limited to, antigens, antibodies, therapeutic drugs, narcotics, enzymes, hormones and proteins. In many instances immunoassay has made possible the detection of biological compounds that are present in trace quantities too low for traditional chemical and enzymatic techniques.

The most commonly known immunoassay techniques provide for a determination of the presence and/or concentration of either a specific antigen, a specific antibody or a specific antigen/antibody complex. For example, given a known amount of antibody or antigen, the level of its corresponding antigen or antibody can be determined. When the concentration of antibody or antigen is too small for direct measurement, a label can be affixed to a known fraction of the antibody or antigen. This label, which is present and measurable at the requisite concentration, acts as a marker for the extent of antibody/antigen binding between the unknown antibody or antigen and its complementary antigen or antibody. The distribution of label between the bound and unbound antibody or antigen can then be used to calculate the amount of unknown that was present in the liquid sample.

In an alternative type of immunological assay commonly referred to as a sandwich assay, an antibody is contacted with a sample containing an analyte to cause the analyte to bind to the antibody. This complex is then contacted with a solution of a labeled antibody which reacts with the bound analyte. The amount of bound labeled antibody is directly proportional to the amount of bound analyte.

Devices useful in testing samples containing antibodies are known and examples are disclosed in U.S. Pat. No. 5,591,645, U.S. Pat. No. 4,632,901 and U.S. Pat. No. 4,483,925 all of which are incorporated by reference herein. Currently, antibody containing samples can be tested singly against many different antigens by setting up individual assays in plates. Alternatively, many antibodies can be tested against single antigens using plates with that antigen attached. Single samples can be tested rapidly using membrane based devices.

What is still lacking in the art, however, is a means for incorporating the simple, rapid membrane-based immunoassay techniques with the large sample techniques of microplate assay systems.

SUMMARY OF THE INVENTION

The present invention is directed to an analytical device and a method of its use for determining an analyte in a fluid sample in an immunoassay comprising a lid having a plurality of elements, the elements having openings suitable to allow passage of a fluid therethrough; and a membrane comprising membrane indicator areas wherein the membrane is supported by the lid and covers the openings of the elements and wherein the membrane further comprises an under surface which is in contact with a porous wick wherein the wick comprises a top portion which extends through the openings of the elements and a bottom portion which comprises a zone containing tracer consisting of particulate label having a particulate label binder attached thereto wherein the bottom portion extends downward from the membrane and is in contact with the analyte.

The tracer may comprise a mixture of particulate labels wherein each label has a particulate label binder attached thereto.

The present invention is also directed to an analytical device and a method of its use for determining an analyte in a fluid sample in an immunoassay comprising a lid having a plurality of elements, the elements having openings suitable to allow passage of a fluid therethrough; and a membrane comprising membrane indicator areas wherein the membrane is supported by the lid and covers the openings of the elements and wherein the membrane further comprises an under surface which is in contact with a porous wick wherein the wick comprises a top portion which extends through the openings of the elements and a bottom portion which comprises a first zone containing tracer attached to a particulate label and a second zone containing salt wherein the bottom portion extends downward from the membrane and is in contact with the analyte. The analyte may be the end product of a DNA amplification reaction.

The tracer of the first zone of the porous wick may comprise one or more oligonucleotides attached to a particulate label and the second zone containing salt to induce hybridization. Alternatively, the first and second zones may be combined.

DETAILED DESCRIPTION OF THE INVENTION

Figure 1:
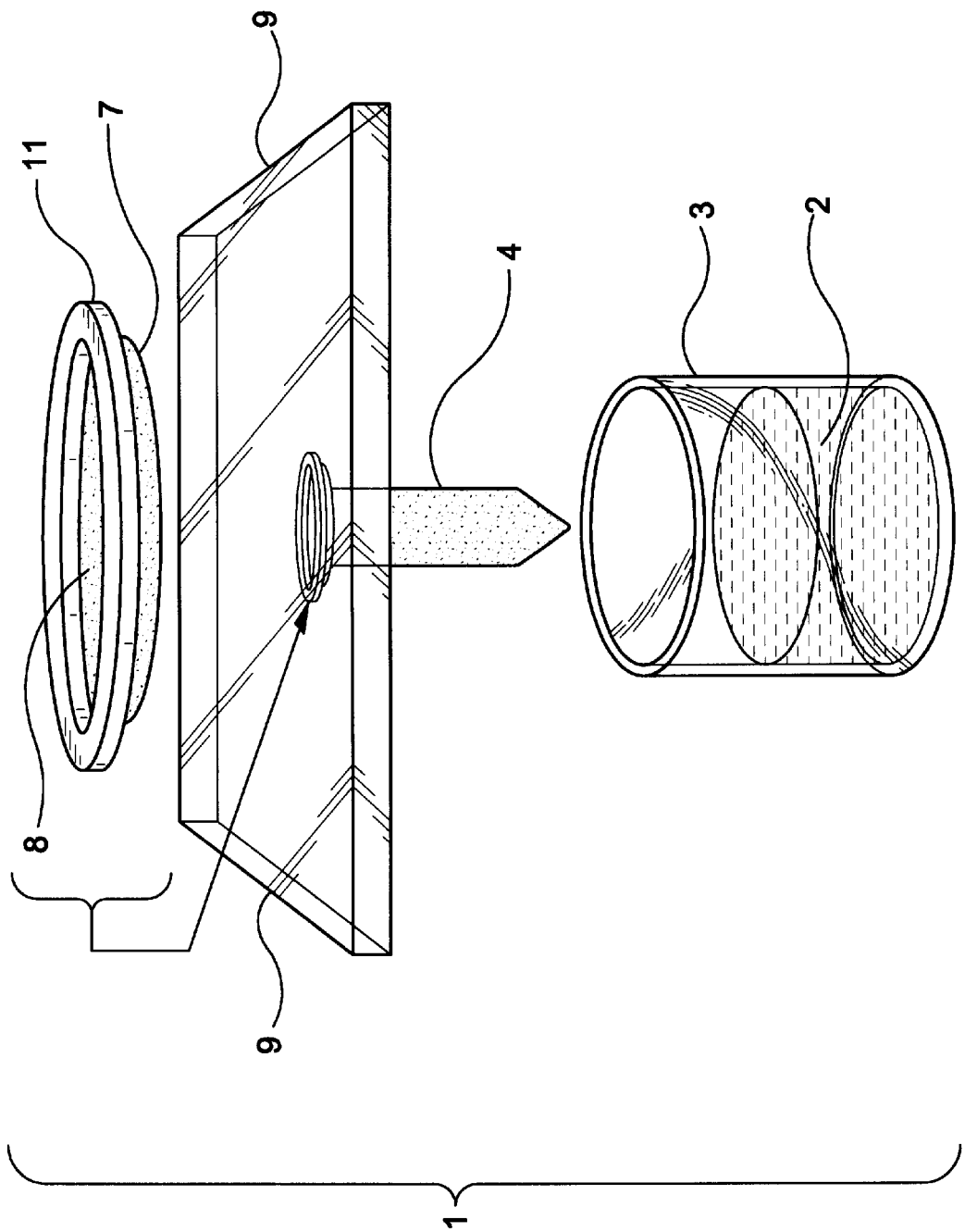
FIG. 1 is a sectional view of a single assay site of the element of the present invention.

While this invention is satisfied by embodiments in many different forms, there is shown in the drawings and will herein be described in detail preferred embodiments of the invention. It is to be understood that the present disclosure is to be considered exemplary of the principles of the invention and is not intended to limit the invention.

Figure 2:
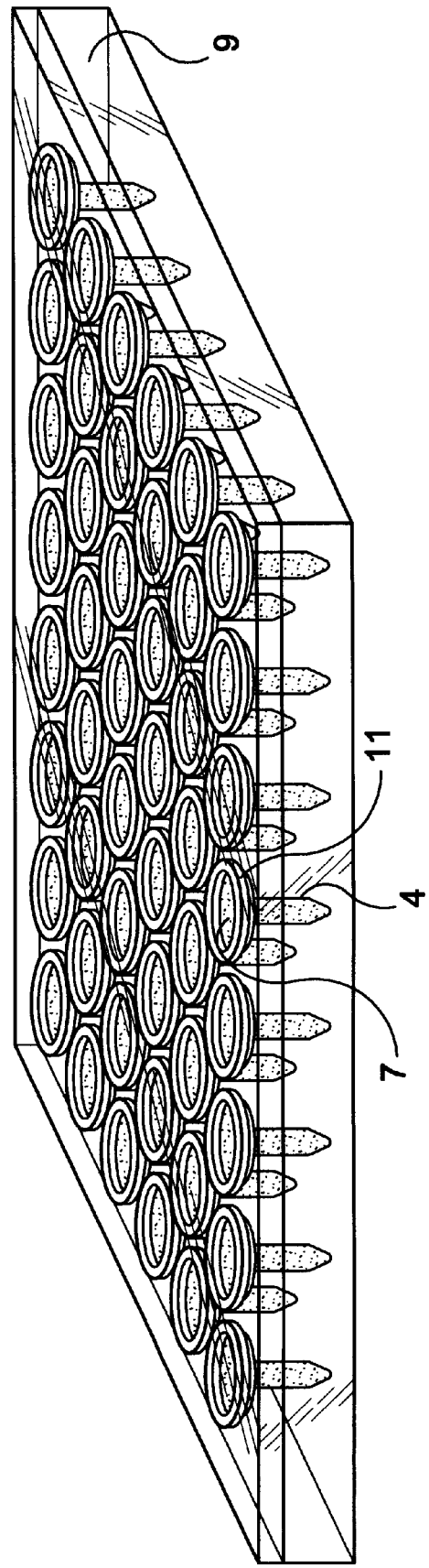
FIG. 2 is a perspective view of the analytical element of the present invention in its use in a 48 well microculture plate.

Referring now to the drawings and to FIG. 1 in particular, there is illustrated a single assay site 1 depicting a single chromatographic immunoassay element of lid 9 of the present invention. A sample to be tested 2 is placed in a well 3. Preferably, the analytical element is used in conjunction with a standard-type well tissue culture plate (such as, for example, 6, 24, 48 and 96-multiwell plates). It can be seen in FIG. 2 that the immunoassay lid 9 has in one embodiment 48 immunoassay units. The lid 9 is preferably a modified plastic culture plate microtiter lid. The immunoassay lid 9 fits on a tissue culture plate with 48 wells.

As can be seen in FIG. 1 attached to the lid 9 is an absorbent paper ring 11. Attached to the ring 11 is a nitrocellulose membrane 7 and which is aligned over the well 3. The membrane 7 contains at least one zone of at least one binder (not shown) at which the reaction color develops (8). In contact with the underside of the membrane 7 is a porous wick 4, which also passes through the openings of the lid 9. The wick 4 suspends downward from the membrane 7, preferably for about 1 cm. The wick 4 is preferably impregnated with colored latex beads (but colloidal gold, other metal particles, polymerized dyes, etc. can also be used). Most preferably, the beads have attached to their surface an antigen.

According to another embodiment, a standard-type 96 well tissue culture plate is utilized with the element of the invention. The tissue culture plate has 96 wells of substantially equal volume and shape. Wells are arranged in orthogonal columns and rows. The volume of the wells may vary according to the needs of the experiment. It is preferred that the tissue culture plate be made of clear, rigid plastic material, although the choice of materials may vary according to requirements.

For the purposes of the present invention, and with reference to FIG. 1, wicking element 4 may be made of a different material than the membrane; the wicking elements may be fabricated together with the membrane or the wicking elements may be subsequently attached to the membrane by any suitable compatible means. However, the embodiment being described, the wicking element and membrane are attached separately, the wicking element is preferably made of porous hydrophilic polyethylene (Porex) and the membrane is preferentially nitrocellulose or nylon.

The wicks are preferably composed of polyethylene, such as Porex. The porous wicks pass through small holes in the lid to contact the membrane and are suspended approximately 1 cm downward. The porous wicks are impregnated with a small amount of colored tracer which is composed of binder for antibody attached to particulate label (such as latex, colloidal gold, polymerized dyes etc.). Particulate label binders on the tracer may be, for example, antigen such as rubella (e.g., Viral Antigens), immunoglobulin, hapten such as biotin (Sigma Chemical Company), therapeutic drugs, drugs of abuse and anti-globulin such as anti-mouse IgG, Protein A (Sigma Chemical Company) and Protein G (Sigma Chemical Company). Attached to the upper surface of the membrane is a ring of absorbent paper centered over each well. The porous membrane contains zone(s) of binder for antibody between the porous wick and the absorbent paper ring. Binder on the porous membrane may be applied just prior to detection of antibody or binder on the membrane may be applied well in advance and stored dry. Binder on the porous membrane may be, for example, antigen or hapten attached to suitable carrier such as bovine serum albumin. Binder on the membrane may also be anti-globulin, Protein A, or Protein G if the tracer is labeled with antigen or hapten.

Detection of antibody is carried out as follows: A lid containing membrane with binder is placed over the corresponding microwell plate containing the samples to be analyzed. During this step, the ends of the porous wicks are immersed in the samples. Sample passes up the porous wick and antibody binds to the tracer. The tracer/antibody complex passes through the wick and into the porous membrane containing zone(s) of binder. If the membrane contains a zone of binder (antigen) specific for the antibody, the tracer/antibody complex binds to the zone of binder resulting in production of color at the zone of binder corresponding to the color of the particular label. If the porous membrane contains more zones of different binders at specific locations, then color development at a specific location identifies the specificity of the antibody in the sample.

Detection of antibody may also be carried out by briefly (approximately 1–4 seconds) placing the lid with porous wicks and membrane over the corresponding microwell plate containing samples. The lid is then transferred to a plate containing buffer which chases the samples up the wicks and into the porous membranes.

Figure 3:
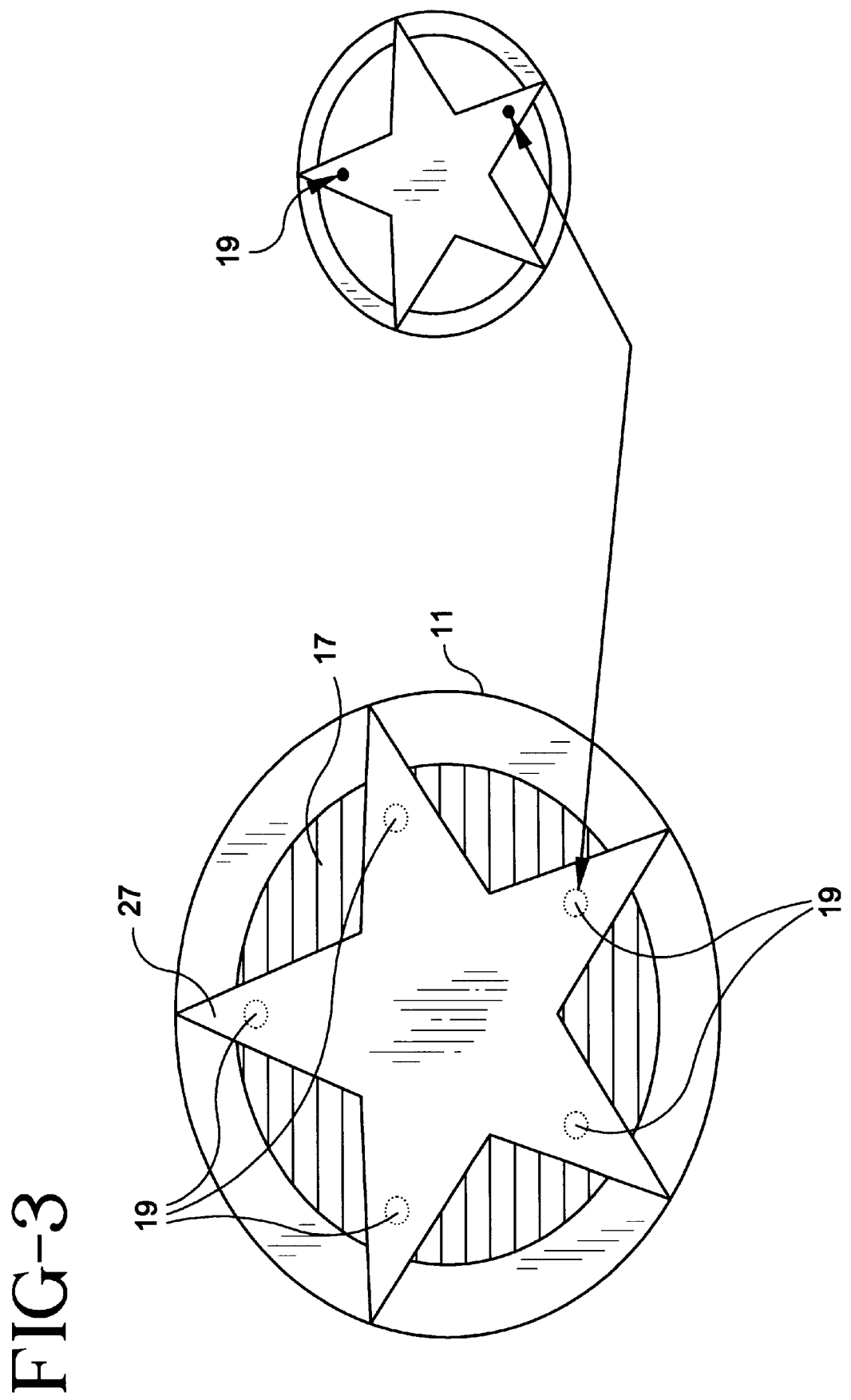
FIG. 3 is a plan view of the element of the present invention showing a chromatographic immunoassay device modified for hybridization.
Figure 4:
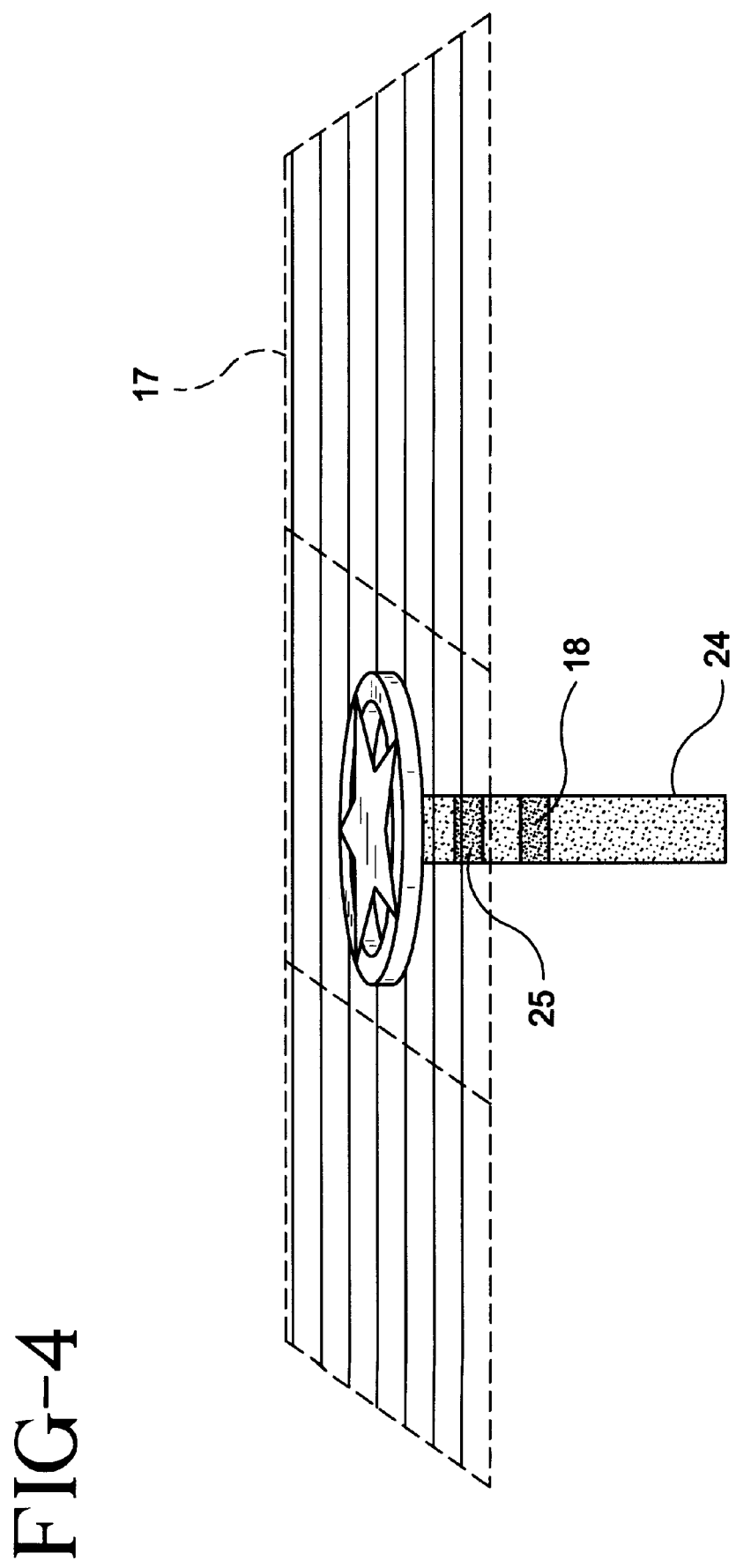
FIG. 4 is a sectional view of the element of the present invention showing a chromatographic immunoassay device modified for hybridization.

The device of the present invention may also be utilized in a technique known as a chromatographic sandwich hybridization assay. Referring now to FIGS. 3 and 4, it can be seen that in an alternative embodiment, the membrane 27 contains several indicator areas 19 in which oligonucleotides are bound. The membrane 27 is attached to absorbent ring 11 which is attached to a lid such as lid 9 in FIG. 1 or a thin plastic support 17 in FIGS. 3 and 4. In contact with the underside of the membrane 27 is a porous wick 24. The porous wick 24 contains a zone of tracer 18 comprising one or more oligonucleotides attached to particulate label and a zone of a salt 25 to induce hybridization. The lid or thin plastic support 17 is placed on the corresponding microwell plate which may contain the end product of a typical DNA amplification reaction. The end products of the amplification may have been denatured by heat or by chemical means such as high pH. The denatured DNA of the sample well passes up the wick 24 and mixes with the tracer. The mixture of tracer and denatured DNA passes through the zone of salt; the denatured DNA hybridizes to the oligonucleotide of the tracer if the sequences are complementary. The tracer with hybridized DNA passes to the oligonucleotide zones 19 on the membrane 27. The tracer/denatured sample DNA complex binds to the oligonucleotide on the membrane if the oligonucleotide on the membrane is complementary to a sequence on the sample DNA. The sequence complementary to the membrane oligonucleotide is distinct from the sequence recognized by the oligonucleotide of the tracer and it is preferable that the sequences of the sample DNA recognized by tracer and membrane oligonucleotides are close in the linear sequence of the sample DNA. The preferred salt to induce hybridization is sodium chloride. Other preferred salts include sodium phosphate, potassium chloride, potassium phosphate and magnesium chloride.

It will be apparent to one skilled in the art that several slightly different variations of the present device may also be employed for the application of different antigens to different locations around the wells. In some other variations of the present device shown in FIG. 4, for example, the first and second zones can be on top of each other and thus combined, or alternatively, the first zone can be above the second zone.

We claim:

1. An analytical device for determining an analyte in a fluid sample in an assay comprising:

a lid having a plurality of elements, said elements having openings suitable to allow passage of a fluid therethrough;

a membrane comprising membrane indicator areas containing binder for said analyte wherein said membrane is supported by said lid and covers the openings of said elements and wherein the membrane further comprises an under surface which is in contact with a porous wick wherein said wick comprises a top portion which extends through the openings of said elements and a bottom portion which comprises a first zone containing tracer which is comprised of binder for said analyte attached to a particulate label, and a second zone containing a salt to induce hybridization, wherein said bottom portion extends downward from said membrane and is in contact with said analyte.

2. The device according to claim 1 wherein said analyte is the end product of a DNA amplification reaction.

3. The device according to claim 1 wherein said binder attached to a particulate label is comprised of oligonucleotides.

4. The device according to claim 3 wherein said particulate label is a latex bead.

5. The device according to claim 1 wherein said binder in the membrane indicator area comprises oligonucleotides.

6. The device according to claim 1 wherein said salt is sodium chloride.

7. The device according to claim 1 wherein said salt is selected from the group consisting of sodium phosphate, potassium chloride, potassium phosphate and magnesium chloride.

8. An analytical device for determining an analyte in a fluid sample in an assay comprising:

a lid having a plurality of elements, said elements having openings suitable to allow passage of a fluid therethrough;

a membrane comprising membrane indicator areas containing binder for said analyte wherein said membrane is supported by said lid and covers the openings of said elements and wherein the membrane further comprises an under surface which is in contact with a porous wick wherein said wick comprises a top portion which extends through the openings of said elements and a bottom portion which comprises a first zone containing tracer which is comprised of binder for said analyte attached to a particulate label and a second zone containing a salt to induce hybridization, wherein said second zone is within said first zone, and further, wherein said bottom portion extends downward from said membrane and is in contact with said analyte.

9. The device according to claim 8 wherein said analyte is the end product of a DNA amplification reaction.

10. The device according to claim 8 wherein said binder attached to a particulate label is comprised of oligonucleotides.

11. The device according to claim 10 wherein said particulate label is a latex bead.

12. The device according to claim 8 wherein said binder in the membrane indicator area comprises oligonucleotides.

13. The device according to claim 8 wherein said salt is sodium chloride.

14. The device according to claim 8 wherein said salt is selected from the group consisting of sodium phosphate, potassium chloride, potassium phosphate and magnesium chloride.

15. An analytical device for determining an analyte in a fluid sample in an assay comprising:

a lid having a plurality of elements, said elements having openings suitable to allow passage of a fluid therethrough;

a membrane comprising membrane indicator areas containing binder for said analyte wherein said membrane is supported by said lid and covers the openings of said elements and wherein the membrane further comprises an under surface which is in contact with a porous wick wherein said wick comprises a top portion which extends through the openings of said elements and a bottom portion which comprises a first zone containing tracer which is comprised of binder for said analyte attached to a particulate label and a second zone containing a salt to induce hybridization, wherein said first zone is above said second zone, and further wherein said bottom portion extends downward from said membrane and is in contact with said analyte.

16. The device according to claim 15 wherein said analyte is the end product of a DNA amplification reaction.

17. The device according to claim 15 wherein said binder attached to a particulate label is comprised of oligonucleotides.

18. The device according to claim 17 wherein said particulate label is a latex bead.

19. The device according to claim 15 wherein said binder in the membrane indicator area comprises oligonucleotides.

20. The device according to claim 15 wherein said salt is sodium chloride.

21. The device according to claim 15 wherein said salt is selected from the group consisting of sodium phosphate, potassium chloride, potassium phosphate and magnesium chloride.

* * * * *